United States Patent [19]

Clauss et al.

[11] Patent Number: 4,468,009
[45] Date of Patent: Aug. 28, 1984

[54] REFRACTORY PROTECTION TUBE FOR IMMERSION MOLTEN METAL DEVICES

[75] Inventors: Harry G. Clauss, Delran, N.J.; John R. Wiese, Dresher, Pa.

[73] Assignee: General Signal Corporation, Stamford, Conn.

[21] Appl. No.: 510,514

[22] Filed: Jul. 5, 1983

[51] Int. Cl.³ .............................................. H01V 1/02
[52] U.S. Cl. ........................................ 266/99; 266/87; 374/140
[58] Field of Search .................. 266/99, 87, 94; 73/304 R, DIG. 9; 374/140, 157; 136/234

[56] References Cited

U.S. PATENT DOCUMENTS 3,505,125  4/1970  Acre .................................... 136/234
3,915,002 10/1975  Hance et al. ..................... 73/DIG. 9
3,950,992  4/1976  Hance ................................. 374/140
4,179,309 12/1979  Hance et al. ....................... 374/140
4,354,382 10/1982  Hagglund ........................ 73/304 R

FOREIGN PATENT DOCUMENTS 0956324  4/1964  United Kingdom ............... 136/234

Primary Examiner—L. Dewayne Rutledge
Assistant Examiner—S. Kastler
Attorney, Agent, or Firm—Harold Huberfeld; Raymond F. MacKay

[57] ABSTRACT

A refractory protection tube for immersion molten metal parameter determining devices having a thin perforated metal tube with a coating of refractory fibers and a binder to provide thermal insulation, freedom from out-gassing and mechanical strength.

7 Claims, 2 Drawing Figures

REFRACTORY PROTECTION TUBE FOR IMMERSION MOLTEN METAL DEVICES

BACKGROUND OF THE INVENTION

This invention relates to protection tubes for the immersion of parameter determining devices into molten metal and more particularly to a non-splash refractory protection tube.

During the refining of metals such as the refining of iron to steel and in the preparation of metals for casting it is essential that certain parameters of the molten metal be accurately and swiftly determined. Some of these parameters are determined by immersing sensing devices into the molten metal that provide electrical signals that are indicative of the magnitude of the parameter. Such sensing devices are used to determine temperature by a thermocouple element, oxygen by an electrochemical cell, and carbon by temperature measurements made as an isolated sample, either in the bath of molten metal or outside the bath, cools through various thermal arrest temperatures. Other parameters of the molten metal require that a sample be removed from the bath of molten metal and be studied by chemical analysis or metallographic analysis. Typical of such parameters are chemical composition and structure.

Parameter determining devices and particularly those that generate electrical signals while immersed in the molten metal are immersed in the molten metal by means of a manipulator consisting of an iron pipe having electrical wires extending therethrough and terminating in appropriate plug-in contact structure at its distal end. During immersion it is essential that the manipulator be physically and thermally protected from the molten metal. In the past this protection has usually been provided by a paper tube of significant wall thickness. Such paper tubes have at least two distinct disadvantages. The paper tube pyrolizes when immersed in high temperature molten metal and thus there is a finite time limit established for the immersion life of the device. Furthermore, the paper tube tends to out-gas and thus produce a hazard to individuals using the devices by causing splashing of the molten metal.

In order to overcome the aforementioned problems a safety sleeve has been used that consists of a metal tube with a castable refractory cement coating applied to the outside of the metal tube. While such a construction eliminated the out-gassing that was present with paper tubes, castable refractory is a relatively poor thermal insulator limiting the useful immersion time of the sensor and, furthermore, such safety sleeves were heavy and expensive.

U.S. Pat. No. 3,816,183 issued June 11, 1974 discusses the problems of the foregoing safety sleeve and proposes an improvement utilizing a paper tube with an outer sleeve made of refractory fibers to provide the non-splash features and the improved thermal insulation necessary to permit more than a single use of a temperature sensing device. The combination of a paper tube and the fibrous sleeve requires that a seal and bond be established between the paper tube and/or the sensor, and the sleeve. Furthermore, the sleeves being made solely of fibrous material and binder have very little mechanical strength and are limited in the lengths available due to the method of manufacture.

SUMMARY OF THE INVENTION

In order to overcome the problems set forth above an improved non-splash insertion device is proposed in which a cylindrical perforated tube is provided as a form with a coating of fibrous refractory material and a binder formed thereon to provide mechanical strength to the resulting product by virtue of the perforated tube and to provide an inert refractory insulator to prevent out-gassing upon immersion in a molten metal bath and to provide sufficient thermal insulation to permit multiple insertion into the molten metal bath without encountering problems resulting from exposure of the body of the parameter detecting device to high temperatures.

It is, therefore, an object of this invention to provide for a parameter detecting device an improved insertion device having a perforated tube or liner upon which is formed a coating of refractory fibers and a binder to provide a nongassing long life insertion device.

BRIEF DESCRIPTION OF THE DRAWINGS

Referring to FIG. 1 the invention is shown as comprising a thin metallic perforated tube 10 with a fibrous refractory coating 14 covering the tube 10 and extending into perforations 12 in the tube 10. Preferably the coating 14 consists of a composition of 50% alumina/50% silica fibers with a suitable binder.

The coating 14 may be readily formed on the outer surface of the tube 10 by immersing the tube 10 into a slurry of refractory fibers and binder in such a way that a partial vacuum may be drawn on the inside of the tube 10. The tube 10 with the coating 14 is then removed from the slurry and allowed to dry. The thickness of the coating 14 on the tube 10 depends upon the consistency of the slurry, the amount of vacuum applied to the inside of the tube 10 and the length of time the vacuum is applied. In practice the thickness of the coating is controlled by each and all of these factors.

Figure 1:
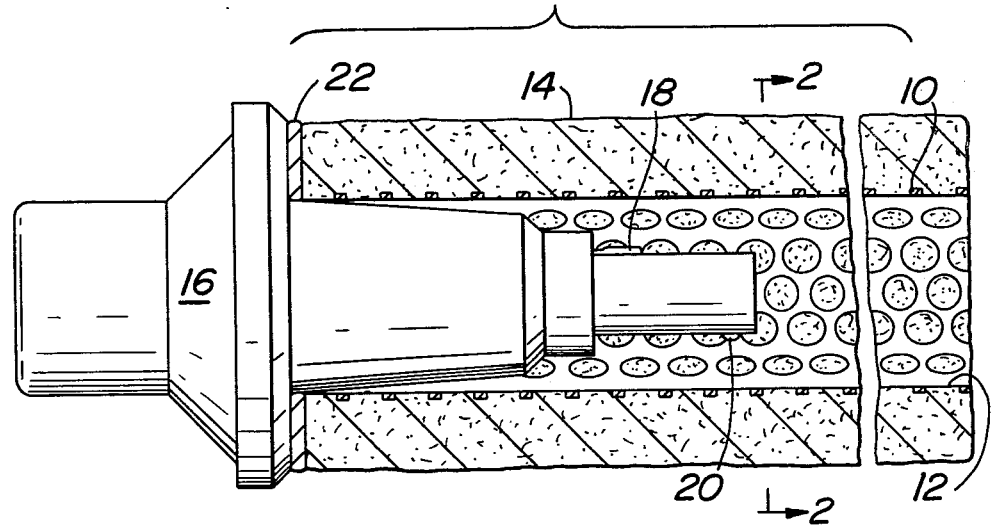
FIG. 1 is a side elevation view in section showing the invention.
Figure 2:
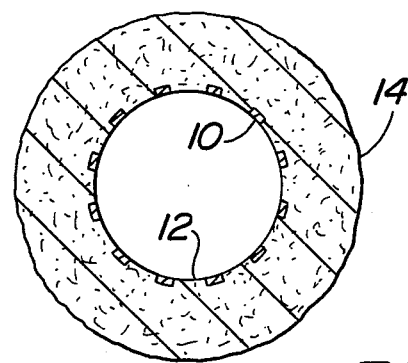
FIG. 2 is an end elevation in section showing the invention.

Referring again to FIG. 1 a parameter determining element 16 is shown in outline form to generically illustrate any one of many different types of elements or devices that may be used with this invention. The element 16 may include a sensing device to produce electrical signals indicative of the parameter being determined and to this end is shown as including electrical contacts 18 and 20. The parameter determining element 16 may be of the type shown in U.S. Pat. No. 3,950,992 having, in addition to a parameter sensing device, sampling cavities for the determination of parameters after the device has been removed from the molten metal.

In practice the parameter determining element 16 is secured to the tube 10 and its coating 14 by a refractory cement 22 that secures the element 16 into the tube 10 and produces a seal with coating 14 to exclude molten metal from entering the tube 10 during immersion. In use the parameter determining element 16 is immersed in a bath of molten metal by means of a pipe or manipulator (not shown) over which is slid the tube 10 until the distal end of the pipe engages and locks with force fit to the parameter determining element 16. If the parameter determining element 16 includes an electrical sensing device then the distal end of the pipe or manipulator includes an electrical contact device to mate with the contacts 18 and 20 of the element 16. It is to be noted that a significant part of the body of the element 16 is thermally protected during immersion by the coating 14 and that the coating 14 will also thermally protect the contacts 18 and 20 and also the pipe or manipulator used to immerse the parameter determining element 16 into the molten metal bath.

The length of pipe or manipulator for immersion of the parameter sensing element 16 that must be thermally protected from the molten metal bath and its environment is determined by the process or application. This invention is particulary advantageous over other fibrous refractory protection tubes because the presence of the perforated tube 10 allows the fabrication of protection tubes of whatever length is required by any application and also provides the finished protection tubes with mechanical strength greater than fibrous protection sleeves that have no liner.

While the perforated tube 10 has been shown as having a wall thickness of approximately one thirty-second of an inch with holes having a diameter of approximately one quarter of an inch and a web separation between holes of approximately one sixteenth of an inch, the size, shape and distribution of the perforations 12 in the tube 10 are not critical as long as the perforations 12 are sufficiently distributed over a substantial portion of tube 10 so that the coating 14 may be readily formed on the outer surface of the tube 10 as described earlier. In one embodiment the tube was made of brass while in another embodiment the tube 10 was constructed of a bronze screen. Any material may be used for the manufacture of the tube 10 provided that the material must be able to withstand the temperatures encountered by immersion in a bath of molten metal.

What is claimed is:

1. An immersion device for immersion in a molten metal to determine a parameter of said molten metal comprising:

a parameter determining element, a tube having a plurality of perforations therein, said perforated tube being adapted to receive said parameter determining element in one end thereof;

a refractory fiber coating formed on the outer surface of said perforated tube said perforations being sufficiently distributed about said tube to permit the formation of said refractory fiber coating by drawing a partial vacuum on the inside of said tube; and means for sealing said parameter determining element to said refractory fiber coating at said one end of said perforated tube.

2. Apparatus as in claim 1 in which said sealing means bonds said parameter determining element to said refractory fiber coating.

3. In an expendable immersion measuring apparatus having a manipulator with electrical leads extending therethrough and terminating at its immersion end in an electrical receptacle connected to said lead and adapted to have the electrical leads from a parameter determining element plugged into said receptacle, the improvement comprising a heat insulating sleeve sealed to said parameter determining element and surrounding a portion of said manipulator said sleeve having a rigid inner surface and an outer coating of refractory fibers adhereing to said rigid inner surface said rigid inner surface having a plurality of perforations therein, said perforations being sufficiently distributed about said rigid inner surface to permit the formation of said refractory fiber coating by drawing a partial vacuum on the inside of said rigid inner surface.

4. Apparatus as claimed in claim 3 in which said rigid perforated inner surface is a perforated metal tube.

5. Apparatus as claimed in claim 3 in which said rigid perforated inner surface is a screen having a fine mesh.

6. Apparatus as claimed in claim 3 in which said parameter determining element is a thermocouple.

7. Apparatus as claimed in claim 3 in which said refractory fibers forming said coating are fibers of alumina and silica.

* * * * *